United States Patent
Araki et al.

(10) Patent No.: US 10,584,367 B2
(45) Date of Patent: Mar. 10, 2020

(54) CELL-SPREADING DEVICE AND METHOD FOR DETECTING RARE CELL

(71) Applicants: Konica Minolta, Inc., Chiyoda-ku, Tokyo (JP); National Institute of Advanced Industrial Science and Technology, Chiyoda-ku, Tokyo (JP)

(72) Inventors: Jungo Araki, Fuchu (JP); Kumiko Hoshi, Tama (JP); Shohei Yamamura, Takamatsu (JP); Shouki Yatsushiro, Takamatsu (JP); Masatoshi Kataoka, Takamatsu (JP)

(73) Assignee: KONICA MINOLTA, INC., Tokyo (JP)

( * ) Notice: Subject to any disclaimer, the term of this patent is extended or adjusted under 35 U.S.C. 154(b) by 0 days.

(21) Appl. No.: 14/411,191

(22) PCT Filed: Jul. 1, 2013

(86) PCT No.: PCT/JP2013/067978
§ 371 (c)(1),
(2) Date: Dec. 24, 2014

(87) PCT Pub. No.: WO2014/007190
PCT Pub. Date: Jan. 9, 2014

(65) Prior Publication Data
US 2015/0337355 A1    Nov. 26, 2015

(30) Foreign Application Priority Data
Jul. 3, 2012    (JP) .................................. 2012-149405

(51) Int. Cl.
*C12Q 1/24* (2006.01)
*B01L 3/00* (2006.01)

(52) U.S. Cl.
CPC .......... *C12Q 1/24* (2013.01); *B01L 3/502761* (2013.01); *B01L 2200/027* (2013.01); *B01L 2200/0652* (2013.01)

(58) Field of Classification Search
CPC .. G01N 15/0272; G01N 15/06; G01N 1/4005; G01N 1/405; G01N 1/4077;
(Continued)

(56) References Cited

U.S. PATENT DOCUMENTS

2006/0073585 A1* 4/2006 McDevitt ................. C12Q 1/04
                                                                    435/288.7
2007/0161051 A1    7/2007 Tsinberg et al.
(Continued)

FOREIGN PATENT DOCUMENTS

JP    2004212048 A1    7/2004
JP    2004330038 A     11/2004
(Continued)

OTHER PUBLICATIONS

Mohamed et al.(Journal of Chromatography A, 1216 (2009) 8289-8295).*

(Continued)

*Primary Examiner* — Sally A Merkling
(74) *Attorney, Agent, or Firm* — Cantor Colburn LLP

(57) ABSTRACT

A cell-spreading device may include a microchamber chip having a microchamber capable of enclosing and retaining a cell, a channel-forming frame united with the microchamber chip to form a channel on the microchamber, an inlet provided in the channel-forming frame to allow a cell suspension to flow into the channel, and an outlet provided in the channel-forming frame to allow the cell suspension, which has been allowed to flow into the channel through the inlet, to flow out from the channel. When an aperture of the microchamber is projected perpendicularly to a longitudinal (Continued)

width of the microchamber chip, the void ratio that is a ratio of the sum total of voids to the longitudinal width is not more than 5%, the void being a length of a portion where the projected aperture of the microchamber is not present against the longitudinal width.

7 Claims, 5 Drawing Sheets

(58) Field of Classification Search
CPC ... G01N 2001/4088; G01N 2015/1493; G01N 15/1484; G01N 2015/0288; G01N 2015/149; B01L 2300/0681; B01L 3/502753; C12M 47/02; C12Q 1/04; C12Q 1/24
See application file for complete search history.

(56) References Cited

U.S. PATENT DOCUMENTS

| | | |
|---|---|---|
| 2007/0264705 A1 | 11/2007 | Dodgson |
| 2012/0122084 A1 | 5/2012 | Wagner et al. |
| 2012/0129208 A1* | 5/2012 | Khine ............... B01L 3/5085 435/29 |
| 2012/0156675 A1* | 6/2012 | Lueerssen ......... B01L 3/50853 435/6.11 |

FOREIGN PATENT DOCUMENTS

| | | |
|---|---|---|
| JP | 2005506083 A | 3/2005 |
| JP | 2005533502 A | 11/2005 |
| JP | 2006262825 A | 10/2006 |
| JP | 2007504816 A | 3/2007 |
| JP | 2011163830 A | 8/2011 |
| WO | 2005023124 A2 | 3/2005 |
| WO | 2010027003 A1 | 3/2010 |
| WO | 2010107497 A2 | 9/2010 |
| WO | 2010135603 A2 | 11/2010 |

OTHER PUBLICATIONS

International Search Report corresponding to Application No. PCT/JP2013/067978; dated Sep. 17, 2013, with English translation.

Matsunaga et al., "High-Efficiency Single-Cell Entrapment and Fluorescence in Situ Hybridization Analysis Using a Poly(dimethylsiloxane) Microfluidic Device Integrated with a Black Poly(ethylene terephthalate) Micromesh", Anal Chem., 2008, 80, pp. 5139-5145.

Written Opinion of the International Searching Authority corresponding to International Application No. PCT/JP2013/067978; dated Sep. 17, 2013, with English translation.

Extended European Search Report corresponding to Application No. 13812976.2-1553/2871232, PCT/JP2013/067978; dated Feb. 2, 2016.

Japanese Notification of Reasons for Refusal corresponding to Application No. 2014-523725; Dispatch Date: Feb. 7, 2017, with English translation.

Japanese Notification of Reason for Refusal corresponding to Application No. 2014-523725; dated Jul. 4, 2017.

European Office Action corresponding to Application No. 13812976.2-1001; dated Sep. 14, 2018.

* cited by examiner

[FIG.1]
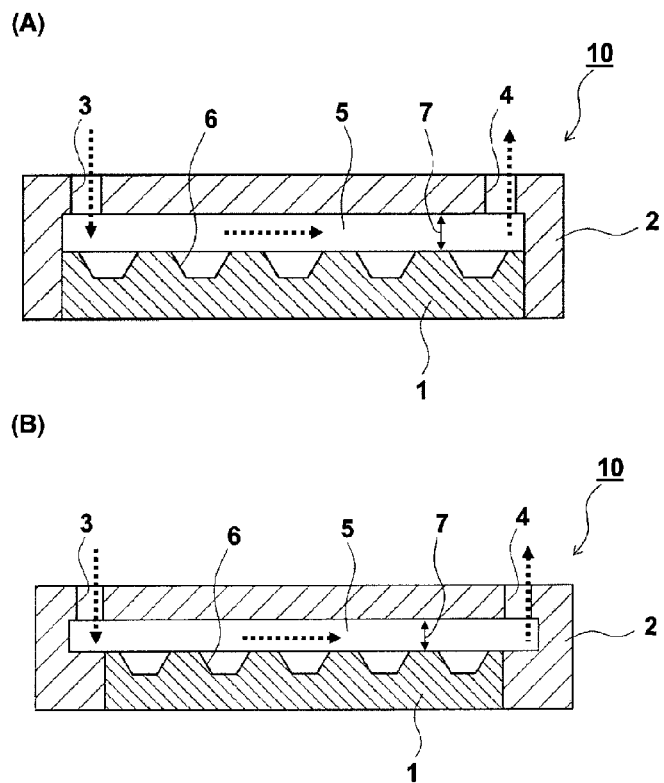
[FIG.2]
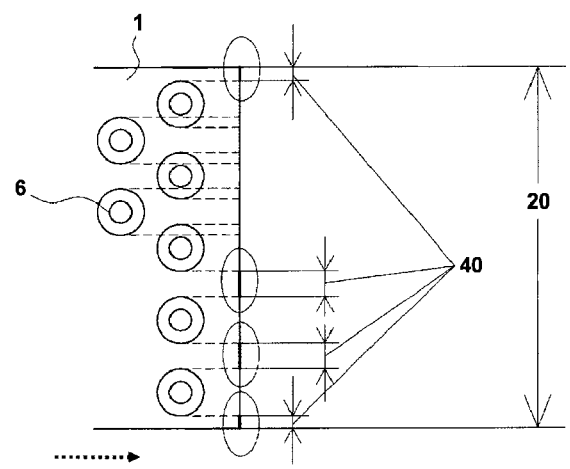

[FIG.3]
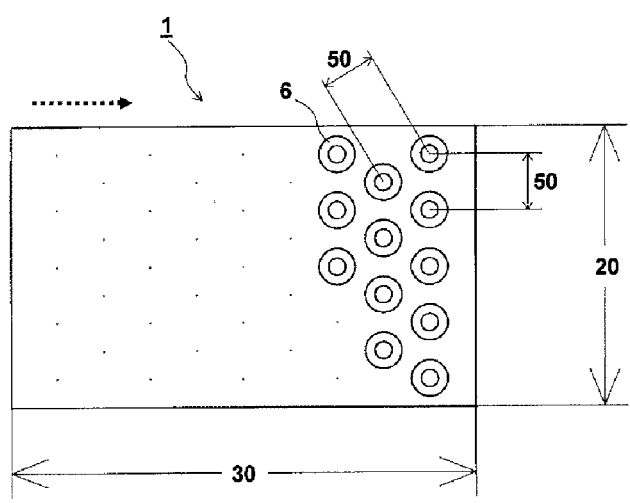

[FIG.4]
(A)
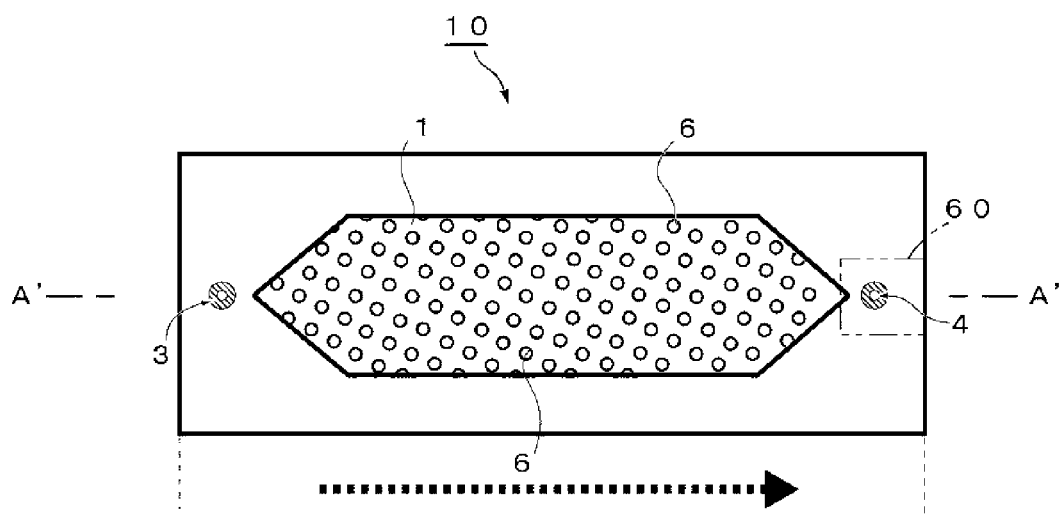
(B)
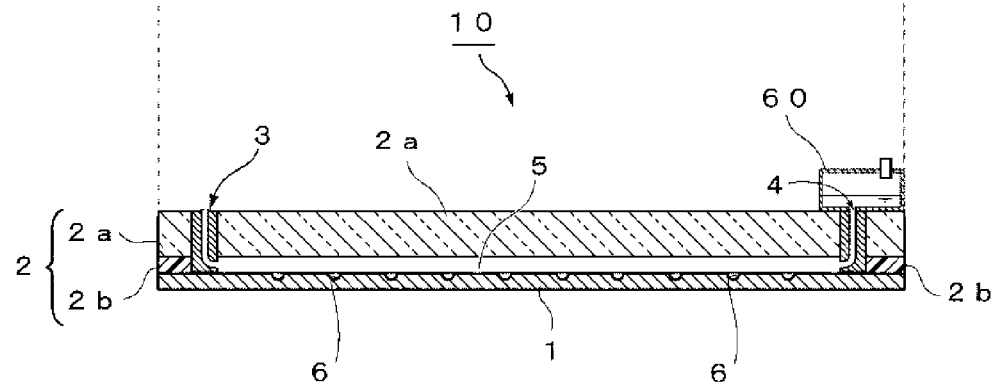

[FIG.5]
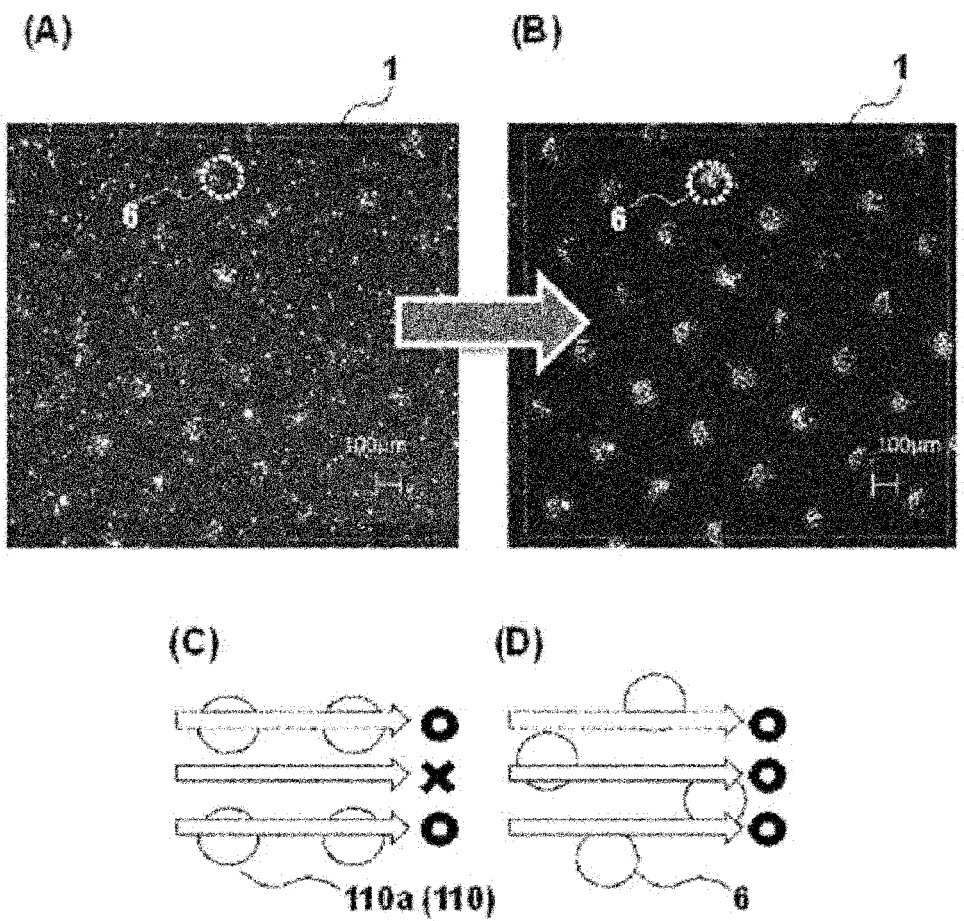

[FIG.6]
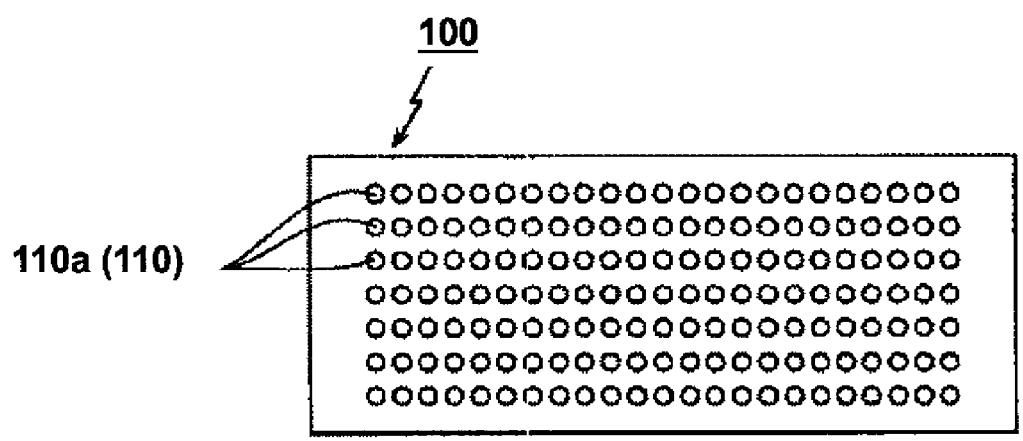
[Fig.7]
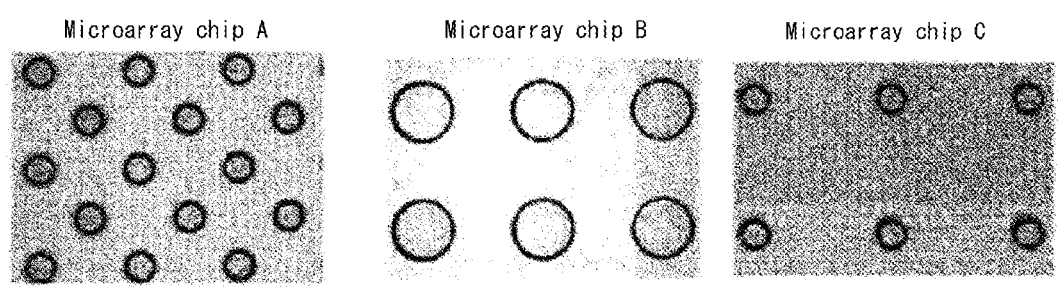

CELL-SPREADING DEVICE AND METHOD FOR DETECTING RARE CELL

The present U.S. patent application is a U.S. National Phase Application under 35 U.S.C. § 371 of International Application PCT/JP2013/067978 filed on Jul. 1, 2013. This application claims a priority under the Paris Convention of Japanese patent application No. 2012-149405 filed on Jul. 3, 2012, the entirety of which is incorporated herein by reference.

TECHNICAL FIELD

The present invention relates to a cell-spreading device comprising a microchamber chip having, on its surface, a microchamber capable of enclosing and retaining a cell, a channel-forming frame, and an inlet and an outlet for a cell suspension that are provided in the channel-forming frame, and a method for detecting a rare cell from a cell suspension by the use of the device.

BACKGROUND ART

In, for example, Cell Research (registered trademark) system approved by the U.S. Food and Drug Administration [FDA] as the CTC [circulating tumor cell] detection that is typical application for detecting rare cells, all cells contained in 7.5 mL of blood are examined, and when 5 or more CTC are found in the case of breast cancer or prostatic cancer or 3 or more CTC are found in the case of colorectal cancer, judgment as positive metastatic breast cancer, prostatic cancer or colorectal cancer is made.

Because the concentration of CTC in blood is extremely low, a high detection power is required for detecting CTC. In the first stage for the detection, it is important that rare cells such as CTC are made to appear in the detection area (e.g., observation visual field of microscope, or the like) with an extremely high probability.

As techniques for detecting cells, several techniques wherein cells are enclosed in a large number of microchambers are known. For example, in a patent literature 1, detection of malaria cells in blood is aimed, and in this detection, large amounts of erythroid cells are fed onto a chip equipped with microchambers each having a well structure, and the detection object is only the erythrocyte enclosed in the wells. FIG. 7 (FIG. 7 of the patent literature 1) shows that, in 3 kinds of microarray chips A to C each of which is equipped with microchambers having specific inner diameters and depths, erythroid cells are enclosed in the microchambers. In each chip, however, the space between the microchambers is large. On that account, it can be easily presumed that when a sample is simply fed onto the microarray chip, large amounts of cells remain outside the microchambers. In addition thereto, such microarray chips are disclosed in patent literatures 2 and 3 and a non patent literature 1.

For example, in the case where the degree of malignancy of breast cancer is intended to be judged from blood of a subject who has been diagnosed with breast cancer by the use of the microarray chip described in the patent literature 1, if 6 CTC are contained in 7.5 mL of the blood and if cells corresponding to 80% of all of the cells fed onto the surface of the microarray chip described in the patent literature 1 can be enclosed in the microchambers, the number of CTC enclosed in the microchambers is 4.8, namely, less than 5. According to the judgment by the Cell Research (registered trademark) system, it is judged to be "negative", and "false negative" occurs.

By the way, when a microchamber type device is intended to be produced in view of industrial mass productivity, molding (or production) using a mold is generally carried out. As a means to improve a ratio of the number of cells enclosed in the microchambers to the number of all of the cells contained in the blood sample, namely, a recovery ratio of cells, a microchamber type device, in which the microchambers are arranged closely to each other, that is, the area outside the microchambers is minimized, can be also considered. However, if it is supposed to "remove" a microchamber type device from a mold during the production using a mold, such a microchamber type device is not realistic, and it is apparent that a certain degree of space becomes necessary between the microchambers.

In order to adopt such a microchamber type device to the detection of rare cells, it is necessary to develop a cell-spreading microchamber device in consideration of a high recovery ratio of cells and efficient mass productivity, namely, capability for production using a mold.

CITATION LIST

Patent Literature

Patent literature 1: WO 2010/027003
Patent literature 2: Japanese Patent Laid-Open Publication No. 2004-212048
Patent literature 3: Japanese Patent Laid-Open Publication No. 2004-330038

Non Patent Literature

Non patent literature 1: High-Efficiency Single-Cell Entrapment and Fluorescence in Situ Hybridization Analysis Using a Poly(dimethylsiloxane) Microfluidic Device Integrated with a Black Poly(ethylene terephthalate) Micromesh Anal. Chem., 2008, 80, 5139-5145

SUMMARY OF INVENTION

Technical Problem

It is an object of the present invention to provide a cell-spreading device which has an extremely high ratio (also referred to as a "recovery ratio of cells" hereinafter) of a total number of cells capable of being retained in microchambers to all of cells contained in a cell suspension containing large amounts of various kinds of cells, such as blood, when the cell suspension is spread onto a microchamber chip surface in the detection of rare cells (e.g., CTC) from the cell suspension, and which has a microchamber chip capable of being mass-produced by a mold.

Solution to Problem

The present inventors have earnestly studied cell-spreading devices for detecting rare cells from a cell suspension. As a result, they have found that the recovery ratio of cells can be remarkably enhanced by allowing a cell suspension to flow on a surface of a microchamber chip having a microchamber arranged under the specific conditions, and they have accomplished the present invention.

That is to say, the cell-spreading device of the present invention that reflects one aspect of the present invention in order to realize at least one of the aforesaid objects is a cell-spreading device (10) comprising at least a microchamber chip (1) having, on its surface, a microchamber (6) capable of enclosing and retaining a cell, a channel-forming frame (2) that is united with the microchamber chip (1) so that a channel (5) may be formed on the microchamber (6), an inlet (3) provided in the channel-forming frame (2) in order to allow a cell suspension to flow into the channel (5), and an outlet (4) provided in the channel-forming frame (2) in order to allow the cell suspension, which has been allowed to flow into the channel (5) through the inlet (3), to flow out from the channel (5), wherein when an aperture of the microchamber (6) is projected perpendicularly to a longitudinal width (20) of the microchamber chip (1), the void ratio that is a ratio of the sum total of voids (40) to the longitudinal width (2) is not more than 5%, said void (4) being a length of a portion where the projected aperture of the microchamber (6) is not present against the longitudinal width (20).

Advantageous Effects of Invention

When the cell-spreading device of the present invention is used and all of cells contained in a cell suspension such as blood are spread onto the microchamber chip, the cells hardly flow out from the outlet of the cell-spreading device and almost all of the cells can be retained in the microchambers. Moreover, such retention can be carried out while maintaining a given space between the microchambers, and therefore, there is no trouble also in the case of production of a microchamber device using a mold.

After the cells are spread, a step of staining rare cells and a washing step subsequent thereto are carried out in order to detect the rare cells, and in such steps, cells remaining on the microchamber chip surface other than the microchamber surface are liable to flow out from the outlet together with a stain solution or a washing liquid. However, even if the staining step or the washing step is carried out, the cells having been enclosed and retained in the microchambers rarely flow out from the outlet because they are retained in the microchambers.

BRIEF DESCRIPTION OF DRAWINGS

FIG. 1 schematically shows sectional views of the cell-spreading device (10) of the present invention, the section of each of said sectional views being parallel with the flow direction of a cell suspension when the cell suspension is allowed to flow in the channel (5). FIG. 1(A) shows an embodiment wherein the bottom face of the channel (5) is constituted of the surface of the microchamber chip (1), and FIG. 1(B) shows an embodiment wherein the bottom face of the channel is constituted of the surface of the microchamber chip (1) and a part of the channel-forming frame (2). Each of the arrows of dotted lines indicates a flow direction of a cell suspension when the cell suspension is allowed to flow into the cell-spreading device (10) of the present invention.

FIG. 2 is a schematic view of a part of an embodiment of the microchamber chip (1) for use in the present invention, said microchamber chip being viewed from directly above, and this figure shows a relationship between a longitudinal width (20) of the microchamber chip (1) and a void (40). The direction indicated by the arrow of a dotted line is as described in FIG. 1.

FIG. 3 is a schematic view of an embodiment of the microchamber chip (1) for use in the present invention, said microchamber chip being viewed from directly above, and a pitch (50) indicates a distance between the centers of adjacent two microchambers (6). Each of dots in this figure represents the same microchamber as the microchamber (6). The direction indicated by the arrow of a dotted line is as described in FIG. 1.

FIG. 4 shows a schematic view 4(A) of a specific embodiment of the cell-spreading device of the present invention overlooked from directly above and a schematic view 4(B) of a section taken on line A'-A' in FIG. 4(A). The direction indicated by the arrow of a dotted line is as described in FIG. 1. On the outlet (4), a reservoir (60) (volume is, for example, 500 µL) is arranged, and the cell suspension having been allowed to flow into through the inlet (3) is discharged from the outlet (4) and temporarily reserved in the reservoir (60). A ceiling and a side face of the channel-forming frame (2) are formed from a channel roof (2a) and a channel seal (2b), respectively.

FIG. 5(A) shows an image of a microchamber chip surface given after the cell suspension is introduced into the channel of the cell-spreading device and allowed to stand still for 5 minutes in Example 1, and FIG. 5(B) shows an image of a microchamber chip surface given after intermittent liquid sending in Example 1. FIG. 5(C) shows an arrangement pattern of recessed portions (110a) (retaining portions (110)) of a plate (100) of a chemical microdevice described in Japanese Patent Laid-Open Publication No. 2004-212048 (patent literature 2), FIG. 5(D) shows an arrangement pattern of microchambers (6) of a microchamber chip (1) used in Example 1, and each of the arrows indicates a route and a direction in which the cells contained in the cell suspension move. In FIGS. 5(C) and 5(D), only the recessed portions (110a) and the microchambers (6) are shown, respectively, but channels are formed on them, and an inlet and an outlet of each channel are present on an extension of a line connecting a tip and an end of the arrow. Therefore, the route and the direction, in which the cell suspension is introduced and is discharged, correspond to the route and the direction indicated by the arrow in each figure.

FIG. 6 is a schematic plan view showing a state where a large number of fine recessed portions (110a) are formed as retaining portions (110) for retaining a sample, on a surface of a plate (100) of a chemical microdevice described in Japanese Patent Laid-Open Publication No. 2004-212048 (patent literature 2) (see FIG. 1 of the publication; reference signs were altered).

FIG. 7 is FIG. 7 described in WO 2010/027003 (patent literature 1), and shows upper surface images of microarray chips A to C having microchambers different in inner diameter and depth, in said microchambers erythroid cells being enclosed.

DESCRIPTION OF EMBODIMENTS

The present invention will be described in detail hereinafter.

Cell-Spreading Device

As shown in, for example, FIG. 1(A), the "cell-spreading device" (10) of the present invention comprises at least a "microchamber chip" (1) having, on its surface, a "microchamber" (6) capable of enclosing and retaining a cell, a "channel-forming frame" (2) that is united with the microchamber chip (1) so that a "channel" (5) may be formed on the microchamber (6), an "inlet" (3) provided in the channel-forming frame (2) in order to allow a cell suspension to flow into the channel (5), and an "outlet" (4) provided in the channel-forming frame (2) in order to allow the cell suspension, which has been allowed to flow into the channel (5) through the inlet (3), to flow out from the channel (5), and as shown in FIG. 2, when an aperture of the microchamber (6) is projected perpendicularly to a "longitudinal width (20) of the microchamber chip (1)", when an aperture of the microchamber (6) is projected perpendicularly to a longitudinal width (20) of the microchamber chip (1) (not a longitudinal width of the channel), the "void ratio" that is a ratio of the sum total of voids (40) to the longitudinal width (2) is not more than 5%, preferably 0%, said void (4) being a length of a portion where the projected aperture of the microchamber (6) is not present against the longitudinal width (20).

As shown in FIG. 3, the "longitudinal width (20) of the microchamber chip (1)" is defined as a width of the microchamber chip (1) in the short direction. On the other hand, the width of the microchamber chip (1) in the long direction is defined as a lateral width (30). In general, the direction in which the cell suspension flows in the channel (that is, direction of a straight line connecting the inlet (3) and the outlet (4)) is a long direction of the microchamber chip, and the longitudinal width (20) of the microchamber chip (1) is a width in the direction perpendicular thereto.

By the use of the cell-spreading device of the present invention, it is also possible to automate a series of steps of spreading the cell suspension onto the microchamber chip, enclosing and retaining cells in the microchamber, and staining and detecting specific rare cells.

Microchamber Chip

The microchamber chip (1) for use in the present invention has, on its surface, one or more microchambers (6) capable of enclosing and retaining one or more cells, and the void ratio is not more than 5%, preferably 0%.

The microchamber in the present invention is an extremely fine concave hole (microwell) capable of "enclosing" and "retaining" one or more cells therein, and preferably has a bottom (that is, preferably not a through hole). Here, "enclosing" means that when a cell suspension is fed onto the surface of the cell-spreading microchamber chip, cells go into (are received in) the microchamber, and "retaining" means that the cells having been enclosed in the microchamber do not go out of the microchamber together with a stain solution, a washing liquid or the like having been fed to the surface of the cell-spreading microchamber chip.

For example, FIG. 5(C) shows an arrangement pattern of recessed portions (11a) (retaining portions (110)) of a hitherto used typical plate (plate of chemical microdevice described in Japanese Patent Laid-Open Publication No. 2004-212048 (patent literature 2)) (100), and in the case where the cells contained in the cell suspension move along routes indicated by the arrows, the cells that go on the recessed portions (11a) are enclosed in the recessed portions (indicated by "○"). However, if the cells do not go on the recessed portions (110a), they pass through the plate (indicated by "×"). The void ratio of this plate is about 50% when visually measured.

On the other hand, for example, FIG. 5(D) shows a preferred arrangement pattern of the microchambers (6) in the present invention, and the void ratio of the microchamber chip having such an arrangement of the microchambers in the transverse direction of the channel is 0% when visually measured. In the case where the cells contained in the cell suspension move along routes indicated by the arrows in FIG. 5(D), the cells go on the microchambers (6) even on any route. Therefore, it can be seen that a possibility that the cells are enclosed in the microchambers (6) is extremely high.

As described above, it can be seen that when the cell suspension is spread on the microchamber chip of the cell-spreading device of the present invention, the ratio (recovery ratio of cells) of the total number of cells capable of being retained in the microchambers to the number of all of the cells contained in the cell suspension is extremely high.

As shown in FIG. 3, the pitch (50) of the microchambers (6) is preferably not less than 1.5 times the diameter of the microchamber (6). In theory, the pitch is preferably as equal to the diameter of the microchamber as possible (that is, the microchambers are preferably in contact with each other), but the microchamber chip (1) is mass-produced using a mold, and therefore, a minimum pitch making it possible to remove the chip from the mold is preferable.

The diameter of the microchamber (6) is preferably 20 to 150 μm. If the diameter of the microchamber exceeds 150 μm, cell retention power of the microchamber tends to be lowered. If the diameter of the microchamber is less than 20 μm, a cell is not enclosed in the microchamber in some cases.

It is preferable to change the depth of the microchamber (6) depending upon the diameter of the microchamber (6), and by a person skilled in the art, the depth of the microchamber can be appropriately determined so that about 10 to 15 cells can be enclosed in one microchamber. Typically, the depth of the microchamber (6) is not less than 20 μm but not more than 100 μm.

In FIGS. 1 to 3, the shape of the microchamber (6) is an inverse conical shape having a flat bottom (vertical section shows a trapezoid), but the present invention is not limited to this embodiment, and for example, cylindrical shape, inverse hemispherical shape, inverse pyramid shape (inverse polygonal pyramid such as inverse quadrangular pyramid or inverse hexagonal pyramid), rectangular parallelepiped, etc. can be mentioned. Although the bottom of the microchamber is typically flat, it may have a curved surface.

As the material of the microchamber chip, the same material as that of a hitherto known microplate or the like can be used, and a material capable of being molded using a mold is preferable. Examples of such materials include polystyrene, polyethylene, polypropylene, polyamide, polycarbonate, polydimethylsiloxane [PDMS], polymethyl methacrylate [PMMA] and a cyclic olefin copolymer [COC]. The microchamber chip may be such a microchamber chip of combined plural materials as is obtained by laminating a substrate made of metal, glass, quartz glass or the like with a molded polymer.

The production process for the microchamber chip (1) may be a process for producing the microchamber chip using a mold having a protruded portion corresponding to the shape of the microchamber (6) on the surface of a substrate, or may be a process for producing the microchamber chip by subjecting a substrate made of the above polymer, metal, glass or the like to direct processing (e.g., fine processing by lithography, drilling, LIGA processing). However, a process for producing the microchamber chip using a mold is preferable.

The microchamber chip (1) may be subjected to a surface treatment, when needed. Examples of the surface treatments include plasma treatment (oxygen plasma treatment or the like), corona discharge treatment and coating treatment with hydrophilic polymer, protein, lipid or the like, but the present invention is not limited to those treatments.

Channel

As shown in, for example, FIG. 1(A), the channel (5) formed in the cell-spreading device (10) of the present invention has a bottom face that is a surface of the microchamber chip (1) and a side face and a ceiling which are formed by the channel-forming frame (2) that is provided so as to be united with the microchamber chip (1), and the channel serves to allow the cell suspension, which has been introduced through the inlet (3) provided in the channel-forming frame (2), to flow therein in the direction of the arrow of a dotted line. Thereafter, the cell suspension is allowed to flow out from the outlet (4) provided in the channel-forming frame (2).

As shown in, for example, FIG. 1(B), the channel (5) may have an embodiment wherein the bottom face is formed from a surface of the microchamber chip (1) and a member other than the microchamber chip (channel-forming frame (2) in FIG. 1(B)). In this case, however, in order to prevent loss of cells due to flow of the cell suspension in the region having no microchamber (1), it is desirable that in the short direction of the microchamber chip (1), the member other than the microchamber chip (1) does not form the bottom face.

Even after the microchamber chip (1) and the channel-forming frame (2) are united with each other, it is possible to separate them from each other. Moreover, it is also possible that after the channel is formed, only the ceiling (channel roof) is removed from the channel-forming frame (2) while remaining the side face only.

The height (7) of the channel (5), that is, a distance between the surface of the microchamber chip (1) other than the surface of the microchamber (6) and the ceiling (also referred to as a "height of ceiling" hereinafter) is preferably 50 to 500 μm. When the height of ceiling is in the above range, it is easy to move cells adhering to the surface of the microchamber chip (1) other than the surface of the microchamber (6) by the power of a water stream, and the time required for sedimentation of cells on the surface of the microchamber chip (1) can be shortened. Moreover, since clogging of the channel with cells, or the like rarely occurs, the cells are smoothly spread, so that such a height is preferable.

The material of the channel-forming frame (2) is, for example, the same material as such a material of the microchamber chip (1) as described above, and it is preferable to use the same material as that of the microchamber chip (1). The channel-forming frame (2) may be subjected to the same surface treatment as such a surface treatment for the microchamber chip (1) as described above.

As shown in, for example, FIG. 4(B), in the channel (5), a silicon sheet both surfaces of which have stickiness, namely, a channel seal (2b), is sandwiched between the channel roof (2a) and the microchamber chip (1), whereby the channel-forming frame (2) can be formed.

Cell Suspension

The cell suspension is, for example, blood such as human blood, lymph, tissue fluid, coelomic fluid or the like, which has a possibility of containing a rare cell, and it may be appropriately diluted with a diluting liquid or the like. The cell suspension is not limited to that of biological origin, and it may be a dispersion of cells, which is artificially prepared by suspending cells for the purpose of tests, researches, etc.

The rare cell is, for example, a cancer cell. Particularly when the cell suspension is blood or a sample of blood origin, the rare cell may be CTC [circulating tumor cell or circulating cancer cell]. The diameters of various cells contained in such a cell suspension are each preferably 10 to 100 μm.

Method for Detecting Rare Cell

According to, for example, FIG. 1(A), the method for detecting a rare cell of the present invention is a method wherein a rare cell having a possibility of being contained in a cell suspension is detected from the cell suspension by the use of the above-mentioned cell-spreading device (10), and the method comprises at least a step of introducing the cell suspension into the channel (5) through the inlet (3) of the cell-spreading device (10) to spread cells on the surface of the microchamber chip (1) and a step of enclosing the spread cells in the microchamber (6), and typically comprises the following steps.

Step (a): A physiological salt solution (preferably the same solvent as in the cell suspension used in the step (b)), such as PBS [phosphate buffered saline], is introduced through the inlet (3) of the cell-spreading device (10) to fill the channel (5) with it.

Step (b): A cell suspension is introduced through the inlet (3) so that the physiological salt solution, with which the channel has been filled in the step (a), may be replaced with the cell suspension, whereby the channel (5) is filled with the cell suspension. Simultaneously with introduction of the cell suspension through the inlet (3), the physiological salt solution is discharged from the outlet (4).

Step (c): The cell suspension is allowed to stand still for 1 to 15 minutes (e.g., 5 minutes) to sediment cells contained in the cell suspension. At this time, some cells are enclosed in the microchambers (6), as shown in, for example, FIG. 5(A), but some cells adhere to the microchamber chip (1) surface other then the microchamber (6) surface.

Step (d): When the sectional area of the channel is 1 to 1,000 $mm^2$, the physiological salt solution (preferably the same solvent as that of the cell suspension used in the step (b)) having a volume that is about 1/100 to 1/2 (e.g., 1/50) of the volume of the cell suspension is sent through the inlet (3) at a flow rate of 1 to 1,000 μL/sec (flow rate per second is preferably adjusted so that the flow velocity may become 1 mm/sec or lower), and allowed to stand still for 1 to 30 seconds (e.g., 10 seconds). This step is preferably repeated twice or more, more preferably 10 times. In the case where liquid sending and standing still are repeated in this step, this liquid sending is particularly referred to as "intermittent liquid sending".

As shown in FIG. 5(B), by carrying out the intermittent liquid sending, the cells, which have not been enclosed in the microchambers (6) and have adhered to the surface other than the microchamber (6) surface, are apt to be enclosed in the microchambers (6).

Step (e): A stain solution (e.g., solution of antibody labeled with fluorescent dye) capable of staining specific rare cells only is introduced through the inlet (3), allowed to react with cells under the specific conditions and thereafter discharged from the outlet (4). In order to wash the cells and the interior of the channel (5), a washing step wherein a washing liquid is introduced through the inlet (3) and discharged from the outlet (4) is preferably carried out once or more.

Since the cells are retained in the microchambers (6), they are hardly discharged from the outlet (4) together with the stain solution or the washing liquid. On the other hand, the cells, which have not been retained in the microchambers (6) and have adhered to the microchamber chip surface other than the microchamber (6) surface, are liable to be discharged from the outlet (4) together with the stain solution or the washing liquid (this is referred to as "loss" (losing) of cells).

Step (f): Stained rare cells are detected by microscopic observation or the like.

EXAMPLES

The present invention is further described with reference to the following examples, but it should be construed that the present invention is in no way limited to those examples.

Example 1

A microchamber chip (made of polyethylene and produced using a given mold) having microchambers (6) arranged as shown in FIG. 5(D) was used for a cell-spreading device. The microchambers of the microchamber chip each had a diameter of 100 μm, a depth of 50 μm and an inverse conical shape having a flat bottom. The pitch indicating a distance between the centers of the adjacent microchambers was 200 μm, and the void ratio was 0%. The longitudinal width and the lateral width of the microchamber chip were 25 mm and 70 mm, respectively, and the channel of the cell-spreading device had a height of 100 μm, a width of 15 mm and a length of 40 mm. That is to say, the sectional area of the channel of the cell-spreading device was 1.5 mm$^2$, and the volume of the channel was 60 mm$^3$ (=0.06 mL).

In the first place, the channel of the cell-spreading device was filled with PBS containing 3% by weight of bovine serum albumin [BSA] (also referred to as "3% BSA-containing PBS" hereinafter). Next, 70 μL (about 7×10$^5$ cells) of a cell suspension (cell concentration: 1×10$^7$ cells/mL) in which 0.4% formaldehyde-fixed Jurkat cells had been dissolved in 3% BSA-containing PBS was introduced into the channel through the inlet under the flow rate conditions of 0.05 mL/min (=50 μL/min) and allowed to stand still for 5 minutes, whereby most of PBS with which the channel had been filled was discharged from the outlet.

An enlarged image of the surface of the microchamber chip at this time is shown in FIG. 5(A). The cells were scattered and sedimented inside and outside the microchambers. Thereafter, intermittent liquid sending (after 1 μL of 3% BSA-containing PBS is sent at a flow velocity of 0.1 mL/min, it is allowed to stand still for 5 seconds) was carried out 10 times.

An enlarged image of the surface of the microchamber chip at this time is shown in FIG. 5(B). Most of the cells that had been scattered outside the microchambers before the intermittent liquid sending could be enclosed in the microchambers. When the number of all of the cells allowed to flow into the cell-spreading device is taken as 100%, the number of cells corresponding to 98% could be enclosed in the microchambers. That is to say, the recovery ratio of cells was 98%.

Example 2

A recovery ratio of cells was determined in the same manner as in Example 1, except that the void ratio of the microchamber chip was changed to 1% or 5%. The intermittent liquid sending was further carried out another 10 times (total: 20 times), and a recovery ratio of cells was determined. The results are set forth in Table 1.

Comparative Example 1

A recovery ratio of cells was determined in the same manner as in Example 1, except that the void ratio of the microchamber chip was changed to 10%. The results are set forth in Table 1.

TABLE 1

|  |  | Recovery ratio of cells (%) | |
| --- | --- | --- | --- |
|  | Void ratio | At the time of completion of 10 times of intermittent liquid sending | At the time of completion of 20 times of intermittent liquid sending |
| Ex. 2 | 1% | 99% | 98% |
|  | 5% | 94% | 98% |
| Comp. Ex. 1 | 10% | 88% | 89% |

Comparative Example 2

A recovery ratio of cells was determined in the same manner as in Example 1, except that a plate having a void ratio of 75%, which is shown in FIG. 6, was used. As a result, the recovery ratio of cells at the time of completion of 10 times of intermittent liquid sending was 26%.

REFERENCE SIGNS LIST

1: microchamber chip
2: channel-forming frame
2a: channel roof
2b: channel seal
3: inlet
4: outlet
5: channel
6: microchamber
7: height of channel (5)
10: cell-spreading device
20: longitudinal width of microchamber chip (1)
30: lateral width of microchamber chip (1) (long direction of microchamber chip (1))
40: void (length obtained by subtracting a width corresponding to a projected aperture of the microchamber (6) from a longitudinal width (2) in the case where an aperture of the microchamber (6) is projected perpendicularly to the longitudinal width (20) of the microchamber chip (1))
50: pitch
60: reservoir
100: plate
110: retaining portion
110a: recessed portion

The invention claimed is:
1. A cell-spreading device for use with a cell suspension, the cell-spreading device comprising:
a microchamber chip having, on its surface, a plurality of microchambers structured to enclose and retain a cell, wherein each of the plurality of microchambers has a bottom,
a channel-forming frame that is united with the microchamber chip to form a channel on the microchamber chip,
an inlet provided in the channel-forming frame in order to allow the cell suspension to flow into the channel, and an outlet provided in the channel-forming frame in order to allow the cell suspension, which has been allowed to flow into the channel through the inlet, to flow out from the channel, the microchamber chip including a lateral width and a longitudinal width, the lateral width being in a direction of a straight line connecting the inlet and the outlet, the longitudinal width being perpendicular thereto, the plurality of microchambers being arranged such that, in a projection along the lateral width direction, at least 95% of the longitudinal width of the microchamber chip is covered by the plurality of microchambers;

wherein a pitch of the plurality of microchambers is not less than 1.5 times a diameter of each of the plurality of microchambers, the pitch being defined as a distance between respective centers of adjacent microchambers of the plurality of microchambers;

in the longitudinal width direction of the microchamber chip, a bottom face of the channel is formed by the microchamber chip;

the channel having a channel depth defined between a surface of the channel-forming frame and a surface of the microchamber chip, the surface of the microchamber chip located between adjacent microchambers of the plurality of the microchambers.

2. The cell-spreading device as claimed in claim 1, wherein the plurality of microchambers are arranged such that 100% of the longitudinal width of the microchamber chip is covered by the plurality of the microchambers.

3. The cell-spreading device as claimed in claim 1, wherein a diameter of each of the plurality of microchambers is not less than 20 μm but not more than 150 μm.

4. The cell-spreading device as claimed in claim 1, wherein the height of the channel is not less than 50 μm but not more than 500 μm.

5. A method for detecting a rare cell having a possibility of being contained in a cell suspension, from the cell suspension by the use of a cell-spreading device comprising a microchamber chip having, on its surface, a plurality of microchambers structured to enclose and retain a cell wherein each of the plurality of microchambers has a bottom; a channel-forming frame that is united with the microchamber chip to form a channel on the microchamber chip; an inlet provided in the channel-forming frame in order to allow the cell suspension to flow into the channel, and an outlet provided in the channel-forming frame in order to allow the cell suspension, which has been allowed to flow into the channel through the inlet, to flow out from the channel, the microchamber chip including a lateral width and a longitudinal width, the lateral width begin in a direction of a straight line connecting the inlet and the outlet, the longitudinal width being perpendicular thereto, the microchambers each having a diameter and a pitch, said method comprising:

introducing the cell suspension into the channel through the inlet of the cell-spreading device to spread cells on the surface of the microchamber chip, and enclosing the spread cells in the plurality of microchambers;

wherein the plurality of microchambers are arranged such that, in a projection along the a lateral width direction, at least 95% of the longitudinal width of the microchamber chip is covered by the plurality of microchambers;

wherein a pitch of the plurality of microchambers is not less than 1.5 times a diameter of each of the plurality of microchambers, the pitch being defined as a distance between respective centers of adjacent microchambers of the plurality of microchambers;

in the longitudinal width direction of the microchamber chip, a bottom face of the channel is formed by the microchamber chip; and the channel having a channel depth defined between a surface of the channel-forming frame and a surface of the microchamber chip, the surface of the microchamber chip located between adjacent microchambers of the plurality of the microchambers.

6. The method for detecting a rare cell as claimed in claim 5, wherein the diameter of the cell contained in the cell suspension is not less than 10 μm but not more than 100 μm.

7. The method for detecting a rare cell according to claim 5, which further comprises performing a plurality of cycles of an intermittent liquid sending in which the cell suspension is sent through the inlet and thereafter allowed to stand still for a predetermined period of time in one cycle.

* * * * *